US006475501B1

(12) United States Patent
Kelly et al.

(10) Patent No.: US 6,475,501 B1
(45) Date of Patent: Nov. 5, 2002

(54) ANTIVIRAL COMPOSITIONS FOR TISSUE PAPER

(75) Inventors: Stephen Robert Kelly, Owenton, KY (US); Kamilah Apewaiye Gbadamosi, Cincinnati, OH (US); Geoffrey Eugene Seger, Tunkhannock, PA (US); Kimberly Ann Biedermann, Cincinnati, OH (US); Jeffrey Michael Morgan, Springboro, OH (US); David Frederick Swaile, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/692,629

(22) Filed: Oct. 19, 2000

Related U.S. Application Data

(63) Continuation-in-part of application No. 09/421,131, filed on Oct. 19, 1999, which is a continuation-in-part of application No. 08/969,049, filed on Nov. 12, 1997, now Pat. No. 6,190,625, and a continuation-in-part of application No. 08/868,783, filed on Jun. 4, 1997, now Pat. No. 5,968,539, which is a continuation-in-part of application No. 08/868,695, filed on Jun. 4, 1997, now abandoned, said application No. 09/421,131, is a continuation-in-part of application No. 08/868,982, filed on Jun. 4, 1997, now Pat. No. 6,183,757, said application No. 09/421,131, is a continuation-in-part of application No. 09/323,419, filed on Jun. 1, 1999, which is a continuation-in-part of application No. 08/869,302, filed on Jun. 4, 1997, now abandoned, said application No. 09/421,131, is a continuation-in-part of application No. 09/323,420, filed on Jun. 1, 1999, now Pat. No. 6,106,851, which is a continuation-in-part of application No. 08/869,300, filed on Jun. 4, 1997, now abandoned, said application No. 09/421,131, is a continuation-in-part of application No. 09/323,513, filed on Jun. 1, 1999, now Pat. No. 6,113,933, which is a continuation-in-part of application No. 08/869,071, filed on Jun. 4, 1997, now abandoned, and a continuation-in-part of application No. 08/869,116, filed on Jun. 4, 1997, now Pat. No. 6,197,315, said application No. 09/421,131, is a continuation-in-part of application No. 08/969,057, filed on Nov. 12, 1997, now Pat. No. 6,284,259, which is a continuation-in-part of application No. 08/868,688, filed on Jun. 4, 1997, now abandoned, and a continuation-in-part of application No. 08/868,687, filed on Jun. 4, 1997, now Pat. No. 6,183,673, and a continuation-in-part of application No. 08/868,717, filed on Jun. 4, 1997, now Pat. No. 6,258,368, and a continuation-in-part of application No. 08/869,301, filed on Jun. 4, 1997, said application No. 09/421,131, is a continuation-in-part of application No. 08/967,972, filed on Nov. 12, 1997, now Pat. No. 6,287,577, and a continuation-in-part of application No. 08/868,718, filed on Jun. 4, 1997, now abandoned, said application No. 09/421,131, is a continuation-in-part of application No. 09/323,531, filed on Jun. 1, 1999, now Pat. No. 6,217,887, which is a continuation-in-part of application No. 08/869,303, filed on Jun. 4, 1997, now abandoned, and a continuation-in-part of application No. 08/869,129, filed on Jun. 4, 1997, now Pat. No. 6,210,695, said application No. 09/421,131, is a continuation-in-part of application No. 08/969,077, filed on Nov. 12, 1997, now Pat. No. 6,214,363, and a continuation-in-part of application No. 08/869,117, filed on Jun. 4, 1997, now Pat. No. 6,190,674, said application No. 09/421,131, is a continuation-in-part of application No. 09/420,646, filed on Oct. 19, 1999, and a continuation-in-part of application No. 09/421,084, filed on Oct. 19, 1999, said application No. 09/421,131, is a continuation-in-part of application No. 09/458,750, filed on Dec. 10, 1999, which is a continuation-in-part of application No. 09/421,179, filed on Oct. 19, 1999, now abandoned, said application No. 09/421,131, is a continuation-in-part of application No. 09/643,903, filed on Aug. 21, 2000.

(51) Int. Cl.$^7$ .............................................. A01N 25/34
(52) U.S. Cl. .................................... 424/404; 424/402
(58) Field of Search ................................ 424/402, 404

(56) References Cited

U.S. PATENT DOCUMENTS

| 3,046,196 A | 7/1962 | de Vaulchier ................. 167/65 |
| 3,138,533 A | 6/1964 | Heim et al. .................... 167/84 |
| 3,227,614 A | 1/1966 | Scheuer ........................ 167/84 |
| 3,374,097 A | 3/1968 | Deerfield, III ................. 99/86 |
| 3,817,702 A | 6/1974 | Paulus et al. .................. 8/120 |

(List continued on next page.)

FOREIGN PATENT DOCUMENTS

| FR | 2538238 A1 | 6/1984 |
| JP | 63-305872 | 12/1988 |
| WO | WO 94/04167 | 3/1994 |
| WO | WO 97/27837 | 8/1997 |
| WO | WO 97/46205 | 12/1997 |

OTHER PUBLICATIONS

Gandhi, Chris S. et al, "Cu (II) inhibition of the proton translocation machinery of the influenza A virus M2 protein" J. Biol. Chem (1990), 274 (9), 5474–5482, XP002166284 page 5474, the abstract.
U.S. patent application Ser. No. 09/041,231, Klofta et al., filed Mar. 12, 1998.
U.S. patent application Ser. No. 09/342,777, Deckner et al., filed Jun. 29, 1999.
U.S. patent application Ser. No. 09/421,131, Beidermann et al., filed Oct. 19, 1999.
U.S. patent application Ser. No. 09/420,646, Morgan et al., filed Oct. 19, 1999.
U.S. patent application Ser. No. 09/421,084, Beerse et al., filed Oct. 19,1999.
U.S. patent application Ser. No. 09/421,179, Page et al., filed Oct. 19, 1999.
U.S. patent application Ser. No. 09/458,750, Page et al., filed Dec. 10, 1999.
U.S. patent application Ser. No. 09/643,903, Seger et al., filed Aug. 21, 2000.

*Primary Examiner*—Thurman K. Page
*Assistant Examiner*—S. Howard
(74) *Attorney, Agent, or Firm*—Julia A. Glazer; David K. Mattheis; David M. Weirich

(57) ABSTRACT

This application relates to antiviral tissue paper comprising a water soluble metal ion as an antiviral agent. The water soluble metal ion has at least one hydroxide ion formation constant wherein the hydroxide ion formation constant is at least $10^{12}$. When added to tissue the water soluble metal ion has the ability to kill certain strains of viruses which come into contact with the tissue.

18 Claims, No Drawings

U.S. PATENT DOCUMENTS

| | | | |
|---|---|---|---|
| 3,867,300 A | 2/1975 | Karabinos et al. | 252/106 |
| 4,045,364 A | 8/1977 | Richter | 252/106 |
| 4,355,021 A | 10/1982 | Mahl et al. | 424/28 |
| 4,732,797 A | 3/1988 | Johnson et al. | 428/74 |
| 4,738,847 A | 4/1988 | Rothe et al. | 424/443 |
| 4,764,418 A | 8/1988 | Kuenn et al. | 428/284 |
| 4,767,788 A * | 8/1988 | Diana | 514/574 |
| 4,824,689 A | 4/1989 | Kuenn et al. | 427/2 |
| 4,828,912 A | 5/1989 | Hossain et al. | 428/289 |
| 4,897,304 A | 1/1990 | Hossain et al. | 428/289 |
| 4,975,217 A | 12/1990 | Brown-Skrobot et al. | 252/107 |
| 5,049,440 A * | 9/1991 | Bornhoeft, III et al. | 428/288 |
| 5,236,700 A | 8/1993 | Koslo et al. | |
| 5,539,088 A | 7/1996 | Schumacher et al. | 534/633 |
| 5,607,754 A | 3/1997 | Giles et al. | 428/211 |
| 5,871,763 A | 2/1999 | Luu et al. | 424/402 |
| 5,905,062 A | 5/1999 | Elliott et al. | 510/124 |
| 5,968,539 A * | 10/1999 | Beerse et al. | 424/405 |
| 5,968,853 A | 10/1999 | Kelly et al. | 442/85 |

* cited by examiner

ANTIVIRAL COMPOSITIONS FOR TISSUE PAPER

CROSS REFERENCES TO RELATED APPLICATIONS

This application is a continuation-in-part of U.S. Ser. No. 09/421,131 filed Oct. 19, 1999, which is a continuation-in-part of prior applications Ser. No. 08/868,783, filed on Jun. 4, 1997, granted as U.S. Pat. No. 5,968,539 on Oct. 19, 1999; Ser No. 08/969,049, filed Nov. 12, 1997, granted as U.S. Pat. No. 6,190,625 on Feb. 20, 2001, which is a continuation-in-part of Ser. No. 08/868,695, filed on Jun. 4, 1997 now abandoned; Ser. No. 08/868,982, filed on Jun. 4, 1997 granted as U.S. Pat. No. 6,183,757 on Feb. 6, 2001; Ser. No. 09/323,419, filed on Jun. 1, 1999, which is a continuation-in-part of Ser. No. 08/869,302, filed on Jun. 4, 1997, now abandoned; Ser. No. 09/323,420, filed on Jun. 1, 1999, granted as U.S. Pat. No. 6,106,851 on Aug. 22, 2000, which is a continuation-in-part of Ser. No. 08/869,300, filed on Jun. 4, 1997, now abandoned; Ser. No. 09/323,513, filed on Jun. 1, 1999, granted as U.S. Pat. No. 6,113,933 on Sep. 5, 2000, which is a continuation-in-part of Ser. No. 08/869,071, filed on Jun. 4, 1997, now abandoned; Ser. No. 08/869,116, filed on Jun. 4, 1997, granted as U.S. Pat. No. 6,197,315 on Mar. 6, 2001; Ser. No. 08/969,057, filed on Nov. 12, 1997, granted as U.S. Pat. No. 6,284,259 on Sep. 4, 2001, which is a continuation-in-part of Ser. No. 08/868,688, filed on Jun. 4, 1997, now abandoned; Ser. No. 08/868,687, filed on Jun. 4, 1997, granted as U.S. Pat. No. 6,183,673 on Feb. 6, 2001; Ser. No. 08/868,717, filed on Jun. 4, 1997, granted as U.S. Pat. No. 6,258,368 on Jul. 10, 2001; Ser. No. 08/869,301, filed on Jun. 4, 1997; Ser. No. 08/967,972, filed on Nov. 12, 1997, granted as U.S. Pat. No. 6,287,577 on Sep. 11, 2001, which is a continuation-in-part of Ser. No. 08/868,718, filed on Jun. 4, 1997 now abandoned; Ser. No. 09/323,531, filed on Jun. 1, 1999, granted as U.S. Pat. No. 6,217,887 on Apr. 17, 2001, which is a continuation-in-part of Ser. No. 08/869,303, filed on Jun. 4, 1997 now abandoned; Ser. No. 08/869,129, filed on Jun. 4, 1997, granted as U.S. Pat. No. 6,210,695 on Apr. 3, 2001; Ser. No. 08/969,077, filed on Nov. 12, 1997, granted as U.S. Pat. No. 6,214,363 on Apr. 10, 2001; and Ser. No. 08/869,117, filed on Jun. 4, 1997, granted as U.S. Pat. No. 6,190,674 on Feb. 20, 2001; U.S. Ser. No. 09/420,646 filed Oct. 19, 1999; U.S. Ser. No. 09/421,084 filed Oct. 19, 1999; U.S. Ser. No. 09/458,750 filed Dec. 10, 1999 which is a continuation-in-part of U.S. Ser. No. 09/421,179 filed Oct. 19, 1999 now abandoned; and U.S. Ser. No. 09/643,903 filed Aug. 21, 2000.

TECHNICAL FIELD

This application relates to antiviral tissue paper comprising virucidally effective water soluble metal ions. These water soluble metal ions exhibit at least one hydroxide formation constant having a value of at least $10^{12}$. When added to tissue paper, these water soluble metal ions have the ability to kill certain strains of viruses which come into contact with the tissue. In addition to their antiviral efficacy, these water soluble metal ions are believed to be mild to the skin, thus mitigating the potential for skin irritation. This application further relates to antiviral lotions comprising a virucidally effective amount of one or more water soluble metal ions. A process for making the antiviral tissue paper of this invention is also disclosed.

BACKGROUND OF THE INVENTION

Whether it be a household, workplace, educational facility or any other location where people tend to gather, preventing the spread of germs is a difficult but yet desirable task. For instance, it is well documented that many hours of productive work are lost due to individuals becoming infected with the common cold or influenza virus.

When one suffers from the common cold or influenza virus, one's mucus is the source of a very high concentration of viruses. After the mucus is aerosolized by a sneeze, cough, or other environmental surfaces, the virus within the mucus has the potential to infect other individuals coming into contact with it. Likewise, mucus deposited into a facial tissue also has the potential to infect others if they come in contact with the contaminated tissue. Transfer of this mucus on the tissue to another individual will likely be through accidental or unintentional contact.

As an example of a possible transfer scenario, consider a cold sufferer who accidentally leaves a mucus infected facial tissue on a hard surface of some type. This hard surface might be a kitchen countertop, a bathroom vanity surface, an office desk or some other piece of furniture. Another family member or colleague may accidentally come into contact with the infected mucus after picking up the tissue to throw it away or by contacting the contaminated countertop area. After coming into such contact with the mucus on the tissue, it is very possible for that individual to become infected with the viral condition (i.e., common cold, influenza) especially if the infected mucus comes into contact with that individual's mucosal membranes.

Another transmission scenario is through the disposal of the facial tissues contaminated with the virus containing mucus. After a household waste basket becomes filled with trash containing a high concentration of infected tissues, it obviously needs to be disposed of in some manner. During this transfer of the household trash into another larger disposal unit, the individual transferring the trash may come into contact with the contaminated tissue. Once again, this individual is at a higher risk for contracting the virus. Many other potential modes of virus transmission are possible after the facial tissue has become infected with the mucus.

Furthermore, virus transmission is not the only concern when one has a cold. As is well known, cold and influenza sufferers typically have sore and irritated skin regions associated with the nose and lips. The irritation, inflammation and redness around the nose and lips can have several causes. A prime one is, of course, the sheer necessity of frequently blowing one's nose into he tissue, and wiping the resultant nasal discharge from the nose and surrounding area.

The degree of irritation and inflammation caused by such blowing and wiping is directly proportional to: (1) the surface roughness of the tissue used; (2) the number of times the nose and its surrounding areas are in contact with the tissue; and (3) the irritation potential of any additives applied to the tissue paper. It is thus imperative to use antiviral compositions that are as mild as possible.

U.S. Pat. No. 4,738,847 issued to Rothe et al. on Apr. 19, 1988 purports to teach a three ply cellulosic tissue wherein a virucidal composition is substantially confined to the center ply. The virucidal composition is composed of citric acid and/or malic acid. A surfactant, sodium lauryl sulfate, may also be included.

U.S. Pat. No. 4,828,912 issued to Hossain et al. on May 9, 1989 purports to teach a virucidal composition applied to a tissue. The virucidal composition may include citric, malic, succinic, and/or benzoic acid. A surfactant may also be included.

Both of these suffer from the same drawback. The virucidal compositions are not mild to the skin.

The antiviral agent(s) of the present invention is effective at killing certain strains of viruses such as influenza virus and rhinovirus. Furthermore, the antiviral agents are much less acidic than the above-mentioned carboxylic acid based virucides. When contacted with the skin or aqueous media, these compounds tend to exhibit pH values in the range of 3–5 which is nearer to the pH of human skin than most carboxylic acids. The antiviral efficacy of the above-mentioned carboxylic acids, on the other hand, are substantially reduced as the pH is increased. At pH 4 or greater, very little, if any, immediate antiviral efficacy exists for most organic acids. Without being bound to theory, it is believed that the lower acidity of the present invention renders the products mild to the skin versus the carboxylic acids that are well know in the art.

Furthermore, because the antiviral agent tends to be mild, the potential for skin irritation and stinging in these areas is greatly reduced. As the potential for skin irritation and stinging is reduced, the antiviral agent may be placed on the outer plies of the tissue product whereby it can easily be transferred directly to the skin. Yet further, this allows for more immediate contact of the antiviral agent with the mucosal discharge. Hence, the antiviral agent does not have to be confined to the inner plies of the tissue.

Thus, it is very surprising to find that the water soluble metal ions of the present invention provide a surprising combination of unique properties including immediate antiviral efficacy and mildness.

The benefits of utilizing the tissue product of the present invention include a tissue product that is effective at preventing the spread of certain cold and flu viruses while being comfortable to use.

SUMMARY OF THE INVENTION

The present invention relates to antiviral tissues that are mild to the skin. The antiviral tissue product comprises one or more fibrous ply(ies) and an antiviral composition. The antiviral composition comprises a water soluble metal ion wherein the water soluble metal ion has at least one hydroxide formation constant with a value of at least $10^{12}$. A non-limiting list of suitable water soluble metal ions include aluminum, copper, and mixtures thereof.

Suitable aluminum compounds include but are not limited to aluminum sulfate, potassium aluminum sulfate, aluminum nitrate, aluminum chlorohydrate, aluminum zirconium tetra-chlorohydrex glycene, and combinations thereof. Suitable copper compounds include but are not limited to copper sulfate, copper chloride, copper nitrate, copper acetate, copper bromide, copper iodide, and mixtures thereof.

The antiviral tissue product may also optionally include a lotion. The lotion may also include an antiviral composition.

The present invention also relates to a process for making an antiviral tissue product.

DETAILED DESCRIPTION OF THE INVENTION

As used herein, the term "comprising" means that the various components, ingredients, or steps, can be conjointly employed in practicing the present invention. Accordingly, the term "comprising" encompasses the more restrictive terms "consisting essentially of" and "consisting of."

As used herein, "pyrrolidone carboxylic acid" collectively refers to its stereoisomers and tautomers.

As used herein, "moisture barrier" refers to a means for inhibiting the penetration of moisture through tissue. Suitable moisture barriers are disclosed in commonly assigned U.S. Pat. No. 5,968,853 issued to Kelly et al. on Oct. 19, 1999, U.S. Ser. No. 09/120,828 filed Jul. 22, 1998, and U.S. Ser. No. 09/287,857 filed Apr. 7, 1999, the disclosures of which are incorporated herein by reference.

As used herein, "antiviral agent" refers to something capable of killing viruses such as rhinovirus and influenza.

As used herein, "antiviral composition" refers to a composition which includes one or more antiviral agents.

As used herein, the terms "tissue paper web", "paper web", "web", "paper sheet", "tissue product", and "paper product" all refer to sheets of paper made by a process comprising the steps of forming an aqueous papermaking furnish, depositing this furnish on a foraminous surface, such as a fourdrinier wire, and removing the water from the furnish as by gravity or vacuum-assisted drainage, with or without pressing, and by evaporation.

As used herein the term "multi-ply tissue paper product" refers to a tissue paper comprised of at least two plies. Each individual ply in turn can be comprised of single-layered or multi-layered (stratified) tissue paper webs. The multi-ply structures are formed by bonding together two or more tissue webs such as by gluing or embossing.

As used herein, "carrier" refers to a means for delivering the antiviral composition to the tissue.

As used herein the terms "through air drying" and "blow through drying" refer to a technique of removing water from the web by drying the web with hot air.

As used herein, the terms "mechanical dewatering", "conventional wet pressing", and "conventional felt pressing" all refer to a technique of removing water from the web by mechanically pressing the web with a dewatering felt.

As used herein, "wire side" refers to the side of the paper web which comes in contact with the forming fabric (i.e.; fourdrinier wire) as the paper web is being formed in the wet end of the paper machine.

As used herein, "fabric side" refers to the side of the paper web which does not come in contact with the forming fabric as the paper web is being formed in the wet end of the paper machine.

As used herein, the term "polyhydric alcohol" refers to an alcohol have more than one hydroxide group.

Though the principle use of this invention is in connection with facial tissues, it is also applicable to other disposable paper products including but not limited to: bath tissue, table napkins, toweling, wipes, and other disposable articles and garments. The tissue paper of this invention may be conventionally wet pressed, through air dried, high bulk pattern densified, or high bulk, uncompacted tissue paper.

All percentages, ratios and proportions used herein are by weight unless otherwise specified.

A. Tissue Paper

The present invention is useful with tissue paper in general, including but not limited to conventionally felt-pressed tissue paper; high bulk pattern densified tissue paper; and high bulk, uncompacted tissue paper. It can be of a homogenous or multi-layered construction; and tissue paper products made therefrom can be of a single-ply or multi-ply construction. The tissue paper has a basis weight of between about 10 g/m² and 130 g/m², preferably between about 20 g/m² and 80 g/m², and most preferably between about 25 g/m² and 60 g/m². Unless otherwise specified, all amounts and weights relative to the paper are on a dry basis.

The tissue paper of the present invention comprises at least one fibrous ply and preferably two or more fibrous plies. The fibrous ply may be noncellulosic, preferably cellulosic, or a combination thereof. The fibrous ply may be layered. Each fibrous ply has two sides. Side one of the fibrous ply is oriented toward the user while side two of the fibrous ply is oriented away from the user. An antiviral composition made according to the present invention is applied to one or more of the fibrous plies. The antiviral composition may be applied to side one of the fibrous ply, side two of the fibrous ply, or both sides.

The antiviral composition may be applied uniformly or nonuniformly to the fibrous ply. It may be applied in a continuous pattern or a discontinuous pattern.

A lotion may be optionally applied to one or more of the fibrous plies. The lotion is preferably applied to side one of the fibrous ply. The lotion may optionally contain the antiviral composition of the present invention. A lotion may optionally be applied to one or more of the fibrous plies.

The antiviral tissue may optionally include a polyhydric alcohol to enhance the softness of the antiviral tissue.

Conventionally pressed tissue paper and methods for making such paper are well known in the art. Such paper is typically made by depositing a papermaking furnish on a foraminous forming wire, often referred to in the art as a fourdrinier wire. Once the furnish is deposited on the forming wire, it is referred to as a web. The web is dewatered by pressing the web and drying at elevated temperature. The particular techniques and typical equipment for making webs according to the process just described are well known to those skilled in the art.

In a typical process, a low consistency pulp furnish is provided from a pressurized headbox. The headbox has an opening for delivering a thin deposit of pulp furnish onto the fourdrinier wire (i.e.; forming fabric) to form a wet web. The web is then typically dewatered to a fiber consistency of between about 7% and about 25% (total web weight basis) by vacuum dewatering and further dried by pressing operations wherein the web is subjected to pressure developed by opposing mechanical members, for example, cylindrical rolls.

The dewatered web is then further pressed and dried by a steam drum apparatus known in the art as a Yankee dryer. Pressure can be developed at the Yankee dryer by mechanical means such as an opposing cylindrical drum pressing against the web. Multiple Yankee dryer drums can be employed, whereby additional pressing is optionally incurred between the drums.

The tissue paper structures that are formed are referred to hereafter as conventional wet pressed tissue paper structures. Such sheets are considered to be compacted since the entire web is subjected to substantial mechanical compressional forces while the fibers are moist and are then dried while in a compressed state.

Pattern densified tissue paper is characterized by having a relatively high bulk field of relatively low fiber density and an array of densified zones of relatively high fiber density. The high bulk field is alternatively characterized as a field of pillow regions. The densified zones are alternatively referred to as knuckle regions. The densified zones can be discretely spaced within the high bulk field or can be interconnected, either fully or partially, within the high bulk field. The patterns can be formed in a non-ornamental configuration or can be formed so as to provide an ornamental design(s) in the tissue paper.

Preferred processes for making pattern densified tissue webs are disclosed in U.S. Pat. No. 3,301,746, issued to Sanford et al. on Jan. 31, 1967; U.S. Pat. No. 3,974,025, issued to Ayers on Aug. 10, 1976; U.S. Pat. No. 4,191,609, issued to Trokhan on Mar. 4, 1980; U.S. Pat. No. 4,637,859, issued to Trokhan on Jan. 20, 1987; U.S. Pat. No. 5,364,504, issued to Smurkoski et al. on Nov. 15, 1994; U.S. Pat. No. 5,366,785, issued to Sawdai on Nov. 22, 1994; U.S. Pat. No. 5,529,664, issued to Trokhan et al., on Jun. 25, 1996; U.S. Pat. No. 5,679,222, issued to Rasch et al., on Oct. 21, 1997; the disclosures of which are incorporated by reference.

In general, pattern densified webs are preferably prepared by depositing a papermaking furnish on a foraminous forming wire such as a fourdrinier wire to form a wet web and then juxtaposing the web against an array of supports. The web is pressed against the array of supports, thereby resulting in densified zones in the web at the locations geographically corresponding to the points of contact between the array of supports and the wet web.

The remainder of the web not compressed during this operation is referred to as the high bulk field. This high bulk field can be further dedensified by application of fluid pressure, such as with a vacuum type device or a blow-through dryer, or by mechanically pressing the web against the array of supports.

The web is dewatered, and optionally predried, in such a manner so as to substantially avoid compression of the high bulk field. This is preferably accomplished by fluid pressure, such as with a vacuum type device or blow-through dryer, or alternately by mechanically pressing the web against an array of supports wherein the high bulk field is not compressed. The operations of dewatering, optional predrying and formation of the densified zones can be integrated or partially integrated to reduce the total number of processing steps performed.

Subsequent to formation of the densified zones, dewatering, and optional predrying, the web is dried to completion, preferably still avoiding mechanical pressing. Preferably, from about 8% to about 55% of the tissue paper surface comprises densified knuckles having a relative density of at least 125% of the density of the high bulk field.

The array of supports is preferably an imprinting carrier fabric having a patterned displacement of knuckles that operate as the array of supports that facilitate the formation of the densified zones upon application of pressure. The pattern of knuckles constitutes the array of supports previously referred to.

Suitable imprinting carrier fabrics are disclosed in U.S. Pat. No. 3,301,746, issued to Sanford et al. on Jan. 31, 1967; U.S. Pat. No. 3,473,576, issued to Amneus on Oct. 21, 1969; U.S. Pat. No. 3,573,164, issued to Friedberg et al. on Mar. 30, 1971; U.S. Pat. No. 3,821,068, issued to Salvucci et al. on May 21, 1974; U.S. Pat. No. 3,974,025, issued to Ayers on Aug. 10, 1976; U.S. Pat. No. 4,239,065, issued to Trokhan on Dec. 16, 1980; U.S. Pat. No. 4,528,239, issued to Trokhan on Jul. 9, 1985; U.S. Pat. No. 5,098,522, issued to Smurkoski on Mar. 24, 1992; U.S. Pat. No. 5,275,700, issued to Trokhan on Jan. 4, 1994; U.S. Pat. No. 5,328,565, issued to Rasch et al., on Jul. 12, 1994; U.S. Pat. No. 5,334,289, issued to Trokhan et al. on Aug. 2, 1994; U.S. Pat. No. 5,496,624, issued to Stelljes, Jr. et al., on Mar. 5, 1996; U.S. Pat. No. 5,500,277, issued to Trokhan et al., on Mar. 19, 1996, U.S. Pat. No. 5,628,876, issued to Ayers et al., on May 13, 1997; and U.S. Pat. No. 5,679,222, issued to Rasch et al. on Oct. 21, 1997, the disclosures of which are incorporated by reference.

Preferably, the furnish is first formed into a wet web on a foraminous forming carrier, such as a fourdrinier wire. The web is dewatered and transferred to an imprinting fabric.

The furnish can alternately be initially deposited on a foraminous supporting carrier that also operates as an imprinting fabric. Once formed, the wet web is dewatered and, preferably, thermally predried to a selected fiber consistency from about 40% to about 80%.

Dewatering is preferably performed with suction boxes or other vacuum devices or with blow-through dryers. The knuckle imprint of the imprinting fabric is impressed in the web as discussed above, prior to drying the web to completion. One method for accomplishing this is through application of mechanical pressure. This can be done, for example, by pressing a nip roll that supports the imprinting fabric against the face of a drying drum, such as a Yankee dryer, wherein the web is disposed between the nip roll and drying drum.

Also, preferably, the web is molded against the imprinting fabric prior to completion of drying by application of fluid pressure with a vacuum device such as a suction box, or with a blow-through dryer. Fluid pressure can be applied to induce impression of densified zones during initial dewatering, in a separate, subsequent process stage, or a combination thereof.

Uncompacted, nonpattern-densified tissue paper structures are described in U.S. Pat. No. 3,812,000, issued to Salvucci et al. on May 21, 1974 and U.S. Pat. No. 4,208,459, issued to Becker et al. on Jun. 17, 1980, both of which are incorporated by reference. In general, uncompacted, nonpattern-densified tissue paper structures are prepared by depositing a papermaking furnish on a foraminous forming wire such as a fourdrinier wire to form a wet web, draining the web and removing additional water without mechanical compression until the web has a fiber consistency of at least about 80%, and creping the web.

Water is removed from the web by vacuum dewatering and thermal drying. The resulting structure is a soft but weak, high bulk sheet of relatively uncompacted fibers. Bonding material is preferably applied to portions of the web prior to creping.

Compacted non-pattern-densified tissue structures are commonly known in the art as conventional tissue structures. In general, compacted, non-pattern densified tissue paper structures are prepared by depositing a papermaking furnish on a foraminous wire such as a fourdrinier wire to form a wet web, draining the web and removing additional water with the aid of a uniform mechanical compaction (pressing) until the web has a consistency of about 25%–50%, transferring the web to a thermal dryer such as a Yankee, and creping the web. Overall, water is removed from the web by vacuum, mechanical pressing and thermal means. The resulting structure is strong and generally of singular density, but very low in bulk, absorbency and softness.

Other suitable tissue paper structures and methods of making tissue paper structures useful with the present invention are disclosed in U.S. Pat. No.: 3,994,771, issued to Morgan, Jr. et al. on Nov. 30, 1976; U.S. Pat. No. 4,225,382, issued to Kearney et al on Sep. 30, 1980; U.S. Pat. No. 4,300,981, issued to Carstens et al. on Nov. 17, 1981; U.S. Pat. No. 5,245,025, issued to Trokhan et al. on Sep. 14, 1993; U.S. Pat. No. 5,277,761, issued to Phan et al. on Jan. 11, 1994; U.S. Pat. No. 5,443,691, issued to Phan et al. on Aug. 22, 1995; U.S. Pat. No. 5,503,715, issued to Trokhan et al. on Apr. 2, 1996; U.S. Pat. No. 5,527,428, issued to Trokhan et al. on Jun. 18, 1996; U.S. Pat. No. 5,534,326, issued to Trokhan et al. on Jul. 9, 1996; U.S. Pat. No. 5,614,061, issued to Phan et al. on Mar. 25, 1997; U.S. Pat. No. 5,654,076, issued to Trokhan et al. on Aug. 5, 1997; U.S. Pat. No. 5,804,036, issued to Phan et al. on Sep. 8, 1998; U.S. Pat. No. 5,804,281, issued to Phan et al. on Sep. 8, 1998; U.S. Pat. No. 5,814,188 issued to Vinson et al. on Sep. 29, 1998; and U.S. Pat. No. 5,820,730, issued to Phan et al. on Oct. 13, 1998, the disclosures of which are incorporated herein by reference.

The tissue may also be made according to U.S. Pat. No. 5,411,636 issued to Hermans et al. on May 2, 1995 and EP 677612 published in the name of Wendt et al. on Oct. 18, 1995.

The tissue may be foreshortened, as is known in the art. Foreshortening can be accomplished by creping the paper from a rigid surface, and preferably from a cylinder. A Yankee drying drum is commonly used for this purpose. Creping is accomplished with a doctor blade as is well known in the art. Creping may be accomplished according to commonly assigned U.S. Pat. No. 6,048,938 issued to Neal et al. on Apr. 11, 2000: U.S. Pat. No. 5,942,085 issued to Neal et al. on Aug. 24, 1999; U.S. Pat. No. 5,865,950 issued to Vinson et al. on Feb. 2, 1999; U.S. Pat. No. 4,191,756 issued to Sawdai on May 4, 1980; or U.S. Ser. No. 09/042,936 filed Mar. 17, 1998, the disclosures of which patents are incorporated herein by reference.

Alternatively or additionally, foreshortening may be accomplished via wet microcontraction as taught in commonly assigned U.S. Pat. No. 4,440,597, issued Apr. 3, 1984 to Wells et al., the disclosure of which is incorporated herein by reference.

The papermaking fibers utilized for the present invention will normally include fibers derived from wood pulp. Other cellulosic fibrous pulp fibers, such as cotton, bagasse, jute, etc., can be utilized and are intended to be within the scope of this invention. Synthetic fibers, such as rayon, nylon, polyester, polyethylene, polypropylene fibers, and MICROBAN®, a material manufactured by Microban Products Co. of Huntersville, N.C., can also be utilized in combination with natural cellulosic fibers. One exemplary polyethylene fiber that can be utilized is PULPEX®, available from Hercules, Inc. of Wilmington, Del.

Applicable wood pulps include chemical pulps, such as kraft, sulfite, solvent, and soda pulps, as well as mechanical pulps including, for example, groundwood, thermomechanical pulp and chemically modified thermomechanical pulp. Chemical pulps, however, are preferred since they impart a superior tactile sense of softness to tissue sheets made therefrom. Pulps derived from both deciduous trees (hereafter, also referred to as "hardwood") and coniferous trees (hereafter, also referred to as "softwood") can be utilized. Also useful in the present invention are fibers derived from recycled paper, which can contain any or all of the above categories as well as other non-fibrous materials such as fillers and adhesives used to facilitate the original papermaking.

In addition to papermaking fibers, the papermaking furnish used to make tissue paper structures can have other components or materials added thereto. The types of additives desirable will be dependent upon the particular end use of the tissue sheet contemplated.

For example, in the tissue products of the present invention wet strength is a desirable attribute. Thus, it is desirable to add to the papermaking furnish chemical substances known in the art as "wet strength" resins.

Useful wet strength resins include those that are generally cationic in character. Examples of wet strength resins suitable for providing permanent wet strength generation, include cationic polyamide-epichlorohydrin resins such as those described in U.S. Pat. No. 3,700,623, issued to Keim on Oct. 24, 1972, and U.S. Pat. No. 3,772,076, issued to Keim, on Nov. 13, 1973, both of which are incorporated by reference.

A useful cationic polyamide-epichlorohydrin wet strength resin suitable for use with the present invention is KYMENE® 557H, commercially available from Hercules, Inc. of Wilmington, Del.

Other suitable wet strength resins include latex based wet strength agents or polyacrylamide resins such as those described in U.S. Pat. No. 3,556,932, issued to Coscia et al. on Jan. 19, 1971, and U.S. Pat. No. 3,556,933, issued to Williams et al. on Jan. 19, 1971, both of which are incorporated herein by reference. One commercial source of polyacrylamide resin is American Cyanamid Co. of Stamford, Conn., which markets one such resin under the name of PAREZ® 631 NC.

Other water-soluble cationic resins which may be used in this invention include urea formaldehyde and melamine formaldehyde resins. The more common functional groups of these polyfunctional resins are nitrogen containing groups such as amino groups and methylol groups attached to nitrogen. Polyethylenimine type resins may also be used in the present invention.

The permanent wet strength resin is applied in an amount of from about 0.05% to 10% by weight of the tissue paper, preferably from about 0.1% to 5% by weight of the tissue paper, more preferably from about 0.2% to 2%, and most preferably from about 0.3% to 1% by weight of the tissue paper.

Other chemical additives which may optionally be added to the pulp furnish of the present invention include but are not limited to additives such as: temporary wet strength agents, dry strength agents, fillers, lint control agents, sizing agents and softening agents.

Suitable temporary wet strength agents include those disclosed in commonly assigned U.S. Pat. No. 4,981,557 issued to Bjorkquist on Jan. 1, 1991; U.S. Pat. No. 5,008,344 issued to Bjorkquist on Apr. 16, 1991; U.S. Pat. No. 5,085,736 issued to Bjorkquist on Feb. 4, 1992; U.S. Pat. No. 5,138,002 issued to Bjorkquist on Aug. 11, 1992; U.S. Pat. No. 5,217,576 issued to Van Phan on Jun. 8, 1993; U.S. Pat. No. 5,656,746 issued to Smith et al. on Aug. 12, 1997; U.S. Pat. No. 5,690,790 issued to Headlam et al. on Nov. 25, 1997; U.S. Pat. No. 5,698,688 issued to Smith et al. on Dec. 16, 1997; U.S. Pat. No. 5,760,212 issued to Smith on Jun. 2, 1998; and U.S. Pat. No. 5,262,007 issued to Phan et al. on Nov. 16, 1993, the disclosures of which are incorporated herein by reference.

Other chemical additives which may optionally be added to the pulp furnish of the present invention include but are not limited to additives such as: temporary wet strength agents, dry strength agents, fillers, lint control agents, sizing agents, and softening agents.

Suitable softening agents for use in the present invention include those disclosed in commonly assigned U.S. Pat. No. : 5,059,282 issued to Ampulski et al. on Oct. 22, 1991; U.S. Pat. No. 5,215,626 issued to Ampulski et al. on Jun. 1, 1993; U.S. Pat. 5,217,576 issued to Van Phan on Jun. 8, 1993; U.S. Pat. No. 5,246,545 issued to Ampulski et al. on Sep. 21, 1993; U.S. Pat. No. 5,262,007 issued to Phan et al. on Nov. 16, 1993; U.S. Pat. No. 5,264,082 issued to Phan et al. on Nov. 23, 1993; U.S. Pat. No. 5,415,737 issued to Phan et al. on May 16, 1995; U.S. Pat. No. 5,510,000 issued to Phan et al. on Apr. 23, 1996; U.S. Pat. No. 5,525,345 issued to Warner et al. on Jun. 11, 1996; U.S. Pat. No. 5,538,595 issued to Trokhan et al. on Jul. 23, 1996; 5,543,067 issued to Phan et al. on Aug. 6, 1996; U.S. Pat. No. 5,814,188 issued to Vinson et al. on Sep. 29, 1998, the disclosures of which are incorporated herein by reference.

B. Antiviral Composition

The antiviral composition of the present invention comprises one or more antiviral agents.

1. Water Soluble Metal Ion

The antiviral agent of the present invention comprises a water soluble metal ion. The water soluble metal ion preferably has one or more hydroxide formation constant(s) with a value of at least $10^{12}$, preferably a value of at least about $10^{15}$, and a value of at least about $10^{20}$. While not wishing to be bound by theory, it is believed that the unique properties of the water soluble metal ion in combination with the tissue web render the tissue product of the present invention efficacious against common influenza and cold viruses such as Rhinoviruses.

Furthermore, as these antiviral compositions tend to be mild, the potential for skin irritation and stinging in these areas is greatly reduced. Preferred water soluble metal ions used in the present invention include copper, aluminum, and mixtures thereof.

Copper salts useful in the present invention include but are not limited to copper sulfate, copper chloride, copper nitrate, copper acetate, copper bromide, copper iodide, or mixtures thereof.

Aluminum salts useful in the present invention include but are not limited to alum (aluminum sulfate), potassium alum (potassium aluminum sulfate), aluminum chloride, aluminum nitrate, aluminum chlorohydrate, and aluminum zirconium tetra-chlorohydrex glycene.

A suitable aluminum sulfate for use with the present invention is available from Holland Company, Incorporated of Adams, Massachusetts. A suitable aluminum chlorohydrate for use with the present invention is available from Summit Research Labs of Huguenot, N.Y.

A non-inclusive list of suitable water soluble metal ions and their cumulative hydroxide formation constants are listed in the table below:

| Cumulative Hydroxide Formation Constants for Water Soluble Metal Ions[a] | | | | | |
|---|---|---|---|---|---|
| Water Soluble Metal Ion | log $K_1$ | log $K_2$ | log $K_3$ | log $K_4$ | log $K_5$ | log $K_6$ |
| Aluminum | 9.27 | | | 33.03 | | |
| Antimony(III) | | 24.3 | 36.7 | 38.3 | | |
| Arsenic[as AsO⁺] | 14.33 | 18.73 | 20.60 | 21.20 | | |
| Beryllium | 9.7 | 14.0 | 15.2 | | | |
| Bismuth(III) | 12.7 | 15.8 | | 35.2 | | |
| Cerium(III) | 14.6 | | | | | |
| Cerium(IV) | 13.28 | 26.46 | | | | |
| Chromium(III) | 10.1 | 17.8 | | 29.9 | | |
| Copper(II) | 7.0 | 13.68 | 17.00 | 18.5 | | |
| Gallium | 11.0 | 21.7 | | 34.3 | 38.0 | 40.3 |
| Indium | 9.9 | 19.8 | | 28.7 | | |
| Iron(III) | 11.87 | 21.17 | 29.67 | | | |
| Lead(II) | 7.82 | 10.85 | 14.58 | | | 61.0 |
| Plutonium(IV) | 12.39 | | | | | |
| Tellurium(IV) | | | | 41.6 | 53.0 | 64.8 | 72.0 |
| Thallium(III) | 12.86 | 25.37 | | | | |
| Titanium(III) | 12.71 | | | | | |
| Uranium(IV) | 13.3 | | | | 41.2 | |
| Vanadium(III) | 11.1 | 21.6 | | | | |

-continued

Cumulative Hydroxide Formation Constants for Water Soluble Metal Ions[a]

| Water Soluble Metal Ion | log $K_1$ | log $K_2$ | log $K_3$ | log $K_4$ | log $K_5$ | log $K_6$ |
|---|---|---|---|---|---|---|
| Vanadium(V) [as $VO^{3+}$] | | 25.2 | | 46.2 | 58.5 | |
| Zinc | 4.40 | 11.30 | 14.14 | 17.66 | | |
| Zirconium | 14.3 | 28.3 | 41.9 | 55.3 | | |

[a]Lange's Handbook Of Chemistry, 14th Edition, McGraw-Hill, Inc., 1992

In the compositions of the present invention the water soluble metal ion is present in an amount such that the final water soluble metal ion comprises from about 0.001% to 100% of the antiviral composition by weight, preferably from about 0.01% to 80% of the antiviral composition by weight, and most preferably from about 0.1% to 70% by weight.

2. Optional Organic Acid

An optional organic acid may also be included with the present invention. Optional organic acids suitable for use with the present invention are disclosed in U.S. Ser. No. 09/643,903 filed Aug. 21, 2000, the disclosure of which is incorporated herein by reference.

A preferred optional organic acid is pyrrolidone carboxylic acid. Pyrrolidone carboxylic acid, which is also referred to as pyroglutamic acid has two stereoisomers (D and L). Both stereoisomers are suitable for use in the present invention. Each or mixtures thereof are preferred for use herein. Furthermore, blends of the two stereoisomers may also be used. The L stereoisomer is most preferred.

The D stereoisomer of pyroglutamic acid is also known by the following names: D-Proline, 5-oxo-(+)-2-Pyrrolidone-5-carboxylic acid, (+)-Pyroglutamic acid, (R)-2-Pyrrolidone-5-carboxylic acid, 5-Oxo-D-proline, D-2-Pyrrolidone-5-carboxylic acid, D-Pyroglutamic acid, D-Pyrrolidinonecarboxylic acid, and D-Pyrrolidonecarboxylic acid.

The L stereoisomer of pyroglutamic acid is also known by the following names: L-Proline, 5-oxo-(−)-2-Pyrrolidone-5-carboxylic acid, (−)-Pyroglutamic acid, (5S)-2-Oxopyrrolidine-5-carboxylic acid, (S)-(−)-2-Pyrrolidone-5-carboxylic acid, (S)-2-Pyrrolidone-5-carboxylic acid, (S)-5-Oxo-2-pyrrolidinecarboxylic acid, (S)-Pyroglutamic acid, 2-L-Pyrrolidone-5-carboxylic acid, 2-Pyrrolidinone-5-carboxylic acid, 5-Carboxy-2-pyrrolidinone, 5-Oxo-L-proline, 5-Oxoproline, 5-Pyrrolidinone-2-carboxylic acid, Glutimic acid, Glutiminic acid, L-2-Pyrrolidone-5-carboxylic acid, L-5-Carboxy-2-pyrrolidinone, L-5-Oxo-2-pyrrolidinecarboxylic acid, L-5-Oxoproline, L-Glutamic acid, .gamma.-lactam, L-Glutimic acid, L-Glutiminic acid, L-Pyroglutamic acid, L-Pyrrolidinonecarboxylic acid, L-Pyrrolidonecarboxylic acid, Oxoproline, PCA, Pidolic acid, Pyroglutamic acid, Pyrrolidinonecarboxylic acid, Pyrrolidone-5-carboxylic acid, and Pyrrolidonecarboxylic acid.

The DL form of pyroglutamic acid (a mixture of the D and L stereoisomers) is known by the following names: DL-Proline, 5-oxo-(.+−.)-2-Pyrrolidone-5-carboxylic acid, (.+−.)-Pyroglutamic acid, 5-Oxo-DL-proline, DL-2-Pyrrolidinone-5-carboxylic acid, DL-2-Pyrrolidone-5-carboxylic acid, DL-Pyroglutamate, DL-Pyroglutamic acid, DL-Pyrrolidonecarboxylic acid, and Oxoproline. The DL form is also commercially available under the tradename Ajidew® A 100.

Some of the above-listed stereoisomers are commercially available from UCIB, France via Barnet Products Corp. of Englewood Cliffs, N.J. under the trade name of Pidolidone® and from Ajinomoto Corp., Japan under the trade name of Ajidew® A-100. Metal salts of pyrrolidone carboxylic acid are also commercially available and can produce pyrrolidone carboxylic acid by acidification of the salt solution with mineral or other organic acids.

The most common is sodium pyrrolidone carboxylate from UCIB, France via Barnet Products Corp. of Englewood Cliffs, N.J. under the trade name of Nalidone® and from Ajinomoto Corp., Japan under the trade names of Ajidew® N-50 and Ajidew® NL-50. Other such salts of pyrrolidone carboxylic acid include but are not limited to copper, iron, potassium, aluminum, manganese, and zinc. Other compounds of pyrrolidone carboxylic acid that may be used include arginine PCA, betaine PCA, and lysine PCA.

In addition to pyrrolidone carboxylic acid, other organic acids may be optionally added to the antiviral composition. These include but are not limited to organic acids such as ascorbic acid and other carboxylic acids.

Suitable other carboxylic acids include but are not limited to alpha hydroxy acids such as $C_1$ to $C_{12}$ saturated, unsaturated, or mixtures thereof of carboxylic acids possessing 1 to 4 carboxylic acid groups and having at least one hydroxyl group substituted on the $C_2$ alpha carbon with additional hydroxyl and other functionalities (i.e.; phenyl, amino, alkyl, etc.) optionally bound along the carbon chain and aromatic ring(s). A non-inclusive list of alpha hydroxy acids which may be used includes: 2-hydroxyhexanoic acid, 2-hydroxyoctanoic acid, 2-hydroxydecanoic acid, 2-hydroxydodecanoic acid, 2-hydroxycaprylic acid, citric acid, tartaric acid, mandelic acid, malic acid, glycolic acid, lactic acid, gluconic acid, hydroxycaprylic acid, 2-hydroxypropionic acid, 2-hydroxybutanoic acid, 2-hydroxypentanoic acid, and mixtures thereof.

Other examples of carboxylic acids useful with this invention include beta hydroxy acids such as $C_1$ to $C_{12}$ saturated, unsaturated, aromatic, or mixtures thereof of carboxylic acids possessing 1 to 4 carboxylic acid groups and having at least one hydroxyl group substituted on the $C_3$ beta carbon with additional hydroxyl and other functionalities (i.e.; phenyl, amino, hydroxyl, alkyl, etc.) optionally bound along the carbon chain or aromatic ring(s). A non-inclusive list of beta hydroxy acids useful with this invention includes: 3-hydroxyhexanoic acid, 3-hydroxyoctanoic acid, 3-hydroxydecanoic acid, 3-hydroxydodecanoic acid, 3-hydroxycaprylic acid, salicylic acid, 5-octanoyl salicylic acid, 3-hydroxybutanoic acid, 3-hydroxypentanoic acid, 3-hydroxypropionic acid, and mixtures thereof.

A non-inclusive list of other carboxylic acids useful with this invention includes $C_1$ to $C_{12}$ saturated, unsaturated, aromatic, or mixtures thereof of carboxylic acids possessing 1 to 4 carboxylic acid groups with optional functional groups (i.e.; phenyl, amino, hydroxyl, alkyl, etc.) substituted along the carbon chain or on the aromatic ring(s) such as propionic acid, hexanoic acid, octanoic acid, decanoic acid; $C_1$ to $C_{12}$ carboxylic acids possessing 1 to 4 carboxylic acid groups wherein a hydroxyl group(s) is substituted on carbon number(s) $C_4$ or above such as 4-hydroxyhexanoic acid, 5,6-dihydroxyhexanoic acid, 6-hydroxyhexanoic acid, 4-hydroxyoctanoic acid, 5-hydroxyoctanoic acid, 6-hydroxyoctanoic acid, 6,7,8-trihydroxyoctanoic acid, 8-hydroxyoctanoic acid, 4-hydroxydecanoic acid, 5-hydroxydecanoic acid, 6-hydroxydecanoic acid, 7-hydroxydecanoic acid, 8-hydroxydecanoic acid, 9-hydroxydecanoic acid, 10-hydroxydecanoic acid, 4-hydroxydodecanoic acid, 5-hydroxydodecanoic acid, 6-hydroxydodecanoic acid, 11-hydroxydodecanoic acid, and 12-hydroxydodecanoic acid; benzoic acid; phthalic acid; acetylsalicylic acid; dehydroacetic acid; sorbic acid; succinic acid; glutaric acid; adipic acid; sebacic acid; maleic acid; folic acid; acetic acid; ethylenediaminetetraacetic acid; glycolic acid; and mixtures thereof.

The optional organic acid comprises from about 0.1% to 80% of the antiviral composition by weight, preferably from about 2% to 50%, of the antiviral composition by weight, and more preferably from about 5% to 20% of the antiviral composition by weight.

3. Optional Metal Salts

Optional metal salts which may be added as an optional component of the antiviral composition of the present invention include those disclosed in U.S. Ser. No. 09/421,131 filed Oct. 19, 1999; Ser. No. 09/421,179 filed Oct. 19, 1999; and Ser. No. 09/458,750 filed Dec. 10, 1999, the disclosures of which are incorporated herein by reference.

In the compositions of the present invention, the optional metal salt is present in amount such that the final metal ion preferably comprises from about 0.001% to about 20%, by weight of the composition, more preferably, from about 0.01% to about 10%, and even more preferably from about 0.05% to about 5%.

4. Surfactant(s)

The antiviral composition of the present invention may also include an optional surfactant.

While not wishing to be limited by theory, it is believed that the optional surfactant can aid in solubilizing the lipid shell layer of the enveloped class of viruses. This solubilization of the lipid shell enhances the ability of the antiviral acids to penetrate into the virus structure and deactivate it.

Suitable surfactants include but are not limited to nonionic, cationic, anionic, amphoteric, and zwitterionic surfactants.

Examples of suitable nonionic surfactants include but are not limited to alkoxylated alcohols having an HLB of about 8 to 20 and the following formula:

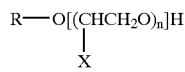

wherein $R=C_2-C_{50}$ and may be either branched, unsaturated, or saturated $n=10-40$ X=hydrogen, methyl, or ethyl A suitable alkoxylated alcohol is polyoxypropylene (5) polyoxyethylene (20) cetyl ether commercially available as PROCETYL AWS manufactured by Croda Incorporated of Parsippany, N.J.

A preferred alkoxylated alcohol is a $C_{12}$ to $C_{15}$ polyethoxylated alcohol commercially available as Tomadol 25-12 from Tomah Products Incorporated of Reserve, Louisiana or as Neodol 25-12 from Shell Chemicals of Houston, Tex. (condensation product of $C_{12}-C_{15}$ linear alcohols with an average of about 12 moles of ethylene oxide).

Other suitable ethoxylated alcohols include TERGITOL 15-S-9 (the condensation product of $C_{11}-C_{15}$ linear alcohols with an average of about 9 moles of ethylene oxide), marketed by Union Carbide Corporation of Danbury, Conn.; and NEODOL 23–6.5T (condensation product of $C_{12}-C_{13}$ linear alcohols with an average of about 6.5 moles of ethylene oxide that has been distilled (topped) to remove certain impurities), and the PLURAFAC brand name surfactants marketed by BASF Corp. of Mount Olive, N.J., such as PLURAFAC A-38 (a condensation product of a $C_{18}$ straight chain alcohol with an average of about 27 moles of ethylene oxide).

Other examples of ethoxylated alcohol surfactants are supplied by Imperial Chemical Company (ICI) of Wilmington, Del. These include the class of BRIJ surfactants and mixtures thereof, such as BRIJ 76 (i.e., Steareth-10) and BRIJ 56 (i.e., Ceteth-10).

Other suitable nonionic surfactants for use in the present invention include alkylglycosides; alkylglycoside ethers as described in U.S. Pat. No. 4,011,389, issued to Langdon et al. on Mar. 8, 1977; alkylpolyethoxylated esters such as PEGOSPERSE 1000MS, available from Lonza Inc. of Fair Lawn, N.J.; ethoxylated sorbitan mono-, di- and/or tri-esters of $C_{12}-C_{18}$ fatty acids having an average degree of ethoxylation of from about 2 to about 20, preferably from about 2 to about 10, such as TWEEN 60 (sorbitan esters of stearic acid having an average degree of ethoxylation of about 20), TWEEN 20 (sorbitan esters of lauric acid having an average degree of ethoxylation of about 20) and TWEEN 61 (sorbitan esters of stearic acid having an average degree of ethoxylation of about 4).

Another type of suitable surfactant for use in the present invention includes AEROSOL TO, a dioctyl ester of sodium sulfosuccinic acid marketed by Cytec Industries Inc. of West Paterson, N.J.

Still other types of suitable surfactants for use in the present invention, include silicone copolymers such as those made by General Electric of Fairfield, Conn. Suitable silicone copolymers include General Electric's SF 1188 (a copolymer of a polydimethylsiloxane and a polyoxyalkylene ether) and General Electric's SF 1228 (a silicone polyether copolymer).

The optional surfactant comprises from about 0.01% to 10% of the antiviral composition by weight, preferably 0.1% to 5%, and most preferably from about 0.2% to 2%.

Other Optional Components of the Antiviral Tissue

1. Moisture Barrier

The antiviral tissue may optionally include one or more moisture barriers. The optional moisture barrier may be joined, connected to, placed on, or impregnated into the fibrous ply. The antiviral composition may optionally be applied to the moisture barrier.

Preferred moisture barriers and a method for making moisture barriers suitable for use with the present invention are disclosed in commonly assigned U.S. Pat. No. 5,968,853 issued to Kelly et al. on Oct. 19, 1999, U.S. Ser. No. 09/120,828 filed Jul. 22, 1998, and U.S. Ser. No. 09/287,857 filed Apr. 7, 1999, the disclosures of which are incorporated herein by reference.

Suitable moisture barriers are also disclosed in Great Britain 1,599,875 published in the name of Sweens et al. on Oct. 7, 1981 and EP 0144658 published in the name of Endres on Jun. 9, 1985.

Moisture barriers are also disclosed in: U.S. Pat. No. 6,054,020 issued to Goulet et al. on Apr. 25, 2000; WO 97/41301 published in the name of McFarland et al. on Nov. 6, 1997; WO 00/00698 published in the name of Hsu et al. on Jan. 6, 2000; Canada 2,239,927 published in the name of McCullough on Jan. 1, 1999

Suitable methods for joining fibrous plies with one another and/or with one or more moisture barriers include but are not limited to ply bonding such as disclosed in commonly assigned U.S. Pat. No. : 3,414,459 issued to Wells on Dec. 3, 1968; U.S. Pat. No. 3,867,225 issued to Nystrand on Feb. 18, 1975; U.S. Pat. No. 4,481,243 issued to Allen on Nov. 6, 1984; and U.S. Pat. No. 5,294,475 issued to McNeil on Mar. 15, 1994; the disclosure of which are incorporated herein by reference.

2. Optional Polyhydric Alcohol

While not wishing to be limited by theory, it is believed that the optional polyhydric alcohol provides enhanced softness to the antiviral tissue.

Suitable polyhydric alcohols include but are not limited to propylene glycol and preferably glycerine (i.e.; glycerol). Other suitable polyhydric alcohols include butylene glycol; hexylene glycol; 1,2 hexane diol; 1,2 pentane diol; sorbitol; sorbitol esters; polyglycerols; polyglycerol esters; and glycerol ethers (e.g.; butyl glycerol ether, isopropyl glycerol ether, and the like).

The optional polyhydric alcohol may comprise from about 0.1% to 99% of the antiviral composition by weight, preferably from about 5% to 90% of the antiviral composition by weight, and more preferably from about 20% to 80% of the antiviral composition by weight.

3. Water Soluble Film Carrier

The antiviral composition of the present invention may also optionally include a water soluble film carrier. A suitable water soluble film carrier for this purpose is disclosed in U.S. Ser. No. 09/342,777 filed on Jun. 29, 1999 the disclosure of which is incorporated herein by reference.

4. Lotion

The tissue of the present invention may optionally include a lotion. The antiviral composition of the present invention may optionally be included as a component of the optional lotion. If the antiviral composition is included as a component of the lotion, the antiviral composition comprises from about 0.05% to 80% of the lotion by weight, preferably from 0.5% to 70% of the lotion by weight. and more preferably from 5% to 60% of the lotion by weight. If the antiviral composition is included as a component of the lotion, the water soluble metal ion comprises from about 0.001% to 100% of the antiviral composition contained in the lotion by weight, preferably from about 0.01% to 80% of the antiviral composition contained in the lotion by weight, and most preferably from about 0.1% to 70% of the antiviral composition contained in the lotion by weight.

Lotions suitable for this purpose are disclosed in U.S. Pat. No. : 4,112,167 issued to Dake et al. on Sep. 5, 1978; U.S. Pat. No. 4,481,243 issued to Allen on Nov. 6, 1984; U.S. Pat. No. 4,513,051 issued to Lavash on Apr. 23, 1985; U.S. Pat. No. 5,525,345 issued to Warner et al. on Jun. 11, 1996; U.S. Pat. No. 5,716,692 issued to Warner et al. on Feb. 10, 1998; U.S. Pat. No. 5,830,487 issued to Klofta et al. on Nov. 3, 1998; and U.S. Ser. No. 09/041,231 filed Mar. 12, 1998, the disclosures of which are incorporated herein by reference.

Preferred lotions suitable for this purpose are disclosed in U.S. Pat. No.: 5,059,282 issued to Ampulski et al. on Oct. 22, 1991; U.S. Pat. No. 5,164,046 issued to Ampulski et al. on Nov. 17, 1992; U.S. Pat. No. 5,385,643 issued to Ampulski on Jan. 31, 1995; U.S. Pat. No. 5,389,204 issued to Ampulski on Feb. 14, 1995; U.S. Pat. No. 5,814,188 issued to Vinson et al. on Sep. 29, 1998; the disclosures of which are incorporated herein by reference.

Lotions preferred for use with the present invention include polysiloxane based lotions.

Types of polysiloxane materials which are suitable for use in the present invention include polymeric, oligomeric, copolymeric, and other multiple-monomeric siloxane materials. As used herein, the term polysiloxane and silicone are used interchangeably. They shall include all of such polymeric, oligomeric, copolymeric and other multiple-monomeric siloxane materials. Additionally, the polysiloxane can be either a straight chain, a branched chain or have a cyclic structure.

Preferred polysiloxane materials include those having monomeric siloxane units of the following structure:

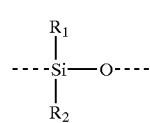

(1)

wherein, $R_1$ and $R_2$ for each siloxane monomeric unit can independently be any alkyl, aryl, alkenyl, alkaryl, aralkyl, cycloalkyl, halogenated hydrocarbon, or other radical. Any of such radicals can be substituted or unsubstituted. $R_1$ and $R_2$ radicals of any particular monomeric unit may differ from the corresponding functionalities of the next adjoining monomeric unit.

Additionally, the radicals can be either a straight chain, a branched chain, or have a cyclic structure. The radicals $R_1$ and $R_2$ can, additionally and independently, be other silicone functionalities such as, but not limited to siloxanes, polysiloxanes, and polysilanes. The radicals $R_1$ and $R_2$ can also contain any of a variety of organic functionalities including, for example, alcohol, carboxylic acid, and amine functionalities.

Preferred polysiloxanes include straight chain organopolysiloxane materials of the following general formula:

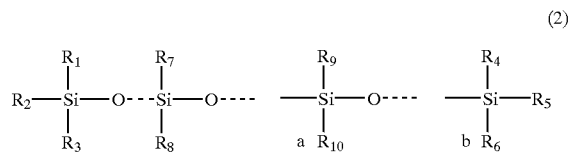

(2)

wherein each $R_1$–$R_9$ radical can independently be any $C_1$–$C_{10}$ unsubstituted alkyl or aryl radical, and $R_{10}$ is any substituted $C_1$–$C_{10}$ alkyl or aryl radical. Preferably each $R_1$–$R_9$ radical is independently any $C_1$–$C_4$ unsubstituted alkyl group. Those skilled in the art will recognize that technically there is no difference whether, for example, $R_9$ or $R_{10}$ is the substituted radical. Preferably the mole ratio of b to (a+b) is between 0 and about 20%, more preferably between 0 and about 10%, and most preferably between about 1% and about 5%.

In one particularly preferred embodiment, $R_1$–$R_9$ are methyl groups and $R_{10}$ is a substituted or unsubstituted alkyl, aryl, or alkenyl group. Such material shall be generally described herein as polydimethylsiloxane which has a particular functionality as may be appropriate in that particular case. Exemplary polydimethylsiloxanes include, for example, polydimethylsiloxane, polydimethylsiloxane having an alkyl hydrocarbon $R_{10}$ radical and polydimethylsiloxane having one or more amino, carboxyl, hydroxyl, ether, polyether, aldehyde, ketone, amide, ester, thiol and/or other $R_{10}$ functionalities including alkyl and alkenyl analogues of such functionalities. For example, an amino functional alkyl group as $R_{10}$ could be an amino-functional or an aminoalkylfunctional polydimethylsiloxane. The exemplary listing of these functional- polydimethylsiloxanes is not meant to thereby exclude others not specifically listed.

A preferred polydimethylsiloxane is CM 849 available from General Electric of Fairfield, Conn.

Viscosity of polysiloxanes useful for this invention may vary as widely as the viscosity of polysiloxanes in general vary, so long as the polysiloxane is flowable or can be made to be flowable for application to the tissue paper. This includes, but is not limited to, viscosity as low as about 25 centistokes to about 20,000,000 centistokes or even higher. High viscosity polysiloxanes which themselves are resistant to flowing can be effectively deposited upon the tissue paper webs by such methods as, for example, emulsifying the polysiloxane in surfactant or providing the polysiloxane in solution with the aid of a solvent, such as hexane, listed for exemplary purposes only. Particular methods for applying polysiloxanes to tissue paper webs are discussed in more detail below.

The optional lotion can be applied to the tissue paper web after the web has been dried, i.e. a "dry web" addition method. The lotion is applied in an amount of from about 0.01% to about 40% by weight of the tissue paper web. Preferably, the lotion is applied in an amount of from about 0.1% to about 25% by weight of the tissue paper web, most preferably from about 0.5% to about 18% by weight of the web.

The lotion can also be applied non-uniformly to the surface(s) of the tissue paper web. As used herein "non-uniform" means that the amount, pattern of distribution, etc. of the lotion can vary over the surface of the paper. For example, some portions of the surface of the tissue paper web can have greater or lesser amounts of lotion, including portions of the surface that do not have any lotion on it.

An example of non-uniform application is where the tissue structure contains differing amounts and differing compositions of various formulations throughout its structure or alternatively where some zones may contain no lotion at all as taught by commonly assigned U.S. Pat. No. 4,481,423 issued to Allen on Nov. 6, 1984 and U.S. Pat. No. 5,814,188 issued to Vinson et al. on Sep. 29, 1998 the disclosures of which are incorporated herein by reference.

For instance in a two ply tissue structure, a lotion containing an antiviral composition might be applied to the two outer surfaces of the paper structure while an antiviral composition is applied to the two inner surfaces of the paper structure. Or in a three ply paper structure, the inside ply might contain the lotion while the user side of the two outside plies contains a skin lotion having an antiviral composition.

Additional examples include adding a lotion not containing any antiviral composition to the outside plies. The lotion might be an ingredient such as dimethicone which would transfer to the skin upon wiping to form a protective layer on the skin. Or, this lotion might transfer another active to the skin such as a sunblock, or skin healing additive.

While this lotion would be applied to the outside plies, the antiviral composition could be applied on the inside of one or both outside plies to produce the antiviral killing activity within the tissue. With the antiviral composition on the inside of the tissue, and the lotion applied to the outside, the antiviral killing activity would most probably be confined to the inside of the tissue rather than the user's skin surface. There are numerous permutations of these approaches.

The lotion can be applied to the tissue paper web at any point after it has been formed. Preferably the lotion is applied after the tissue web has been dried. For example, the lotion can be applied to the tissue paper web after it has been creped from a Yankee dryer, but prior to calendering, i.e., before being passed through calendar rolls. The lotion can also be applied to the paper web after it has passed through such calendar rolls and prior to being wound up on a parent roll. Usually, it is preferred to apply the lotion to the tissue paper as it is being unwound from a parent roll and prior to being wound up on smaller, finished paper product rolls.

The lotions of the present invention may be applied to the tissue paper by spraying the composition onto the tissue paper web or by gravure coating and extrusion coating methods. Gravure coating and extrusion coating methods are preferred such as those taught by U.S. Pat. No. 5,246,546, issued to Ampulski on Sep. 21, 1996 and incorporated herein by reference.

Treating Tissue Paper with Compositions of the Present Invention

In preparing virucidal tissue products according to the present invention, the antiviral composition and the optional lotion (whether the optional lotion includes or does not include an antiviral composition) may be applied to at least one surface of a tissue paper web. They may be applied uniformly or discretely to the tissue paper web. A non-limiting example of discrete addition to the tissue paper web is disclosed in U.S. Pat. No. 5,814,188 issued to Vinson et al. on Sep. 29, 1998, the disclosure of which is incorporated herein by reference.

The antiviral composition and the optional lotion may be applied in a continuous pattern or discontinuous pattern. Suitable application methods include those disclosed in U.S. Pat. No. : 4,481,243 issued to Allen on Nov. 6, 1984; U.S. Pat. No. 5,720,966 issued to Ostendorf on Feb. 24, 1998; and U.S. Pat. No. 5,814,188 issued to Vinson et al. on Sep. 29, 1998, the disclosures of which are incorporated herein by reference.

Suitable methods include spraying, dipping, soaking, printing (e.g., flexographic printing), coating (e.g., gravure coating), extrusion, or combinations of these application techniques, e.g. spraying the composition on a rotating surface, such as a calendar roll, that then transfers the composition to the surface of the paper web. The composition can be applied either to one surface of the tissue paper web, or both surfaces.

The compositions of this invention can also be applied non-uniformly to the surface(s) of the tissue paper web. As used herein "non-uniform" means that the amount, pattern of distribution, etc. of the composition can vary over the surface of the paper. For example, some portions of the surface of the tissue paper web can have greater or lesser amounts of the composition, including portions of the surface that do not have any composition on it.

An example of non-uniform application is where the tissue structure contains differing amounts and differing compositions of various formulations throughout its structure or alternatively where some zones may contain no lotion at all as taught by U.S. Pat. No. 4,481,243 issued to Allen on Nov. 6, 1984 and incorporated herein by reference.

The amount of antiviral composition or lotion containing an antiviral composition that is applied to the tissue is based upon the amount of water soluble metal ion which is added to the tissue on a dry weight basis. The amount of water soluble metal ion applied to the tissue is from about 0.05% to 50% by weight, preferably about 0.1% to 25% by weight, and more preferably from about 0.2% to 15% by weight. The amount of antiviral composition on the paper must be optimized in order to achieve effective inactivation of the virus. The pH of the antiviral tissue paper is about 6 or less, preferably less than about 5, and most preferably less than about 4.

Virucidal Assay Procedure

Protocol Summary

A suspension of high titre Rhinovirus type 14 (hereinafter referred to as "RV-14") is inoculated on a disc of tissue paper which has been previously placed in a Buchner funnel filtration device. The tissue is exposed to the virus for one minute. Immediately following the 1 minute exposure period, the virus aliquot is collected from the tissue by dispensing elution media onto the surface of the tissue and immediately applying vacuum suction. The virus aliquot is collected in a sterilized test tube, titered by 10-fold serial dilution, and assayed for the presence of virus.

The appropriate virus controls, cytotoxicity controls, and neutralization controls are assayed in parallel. Antiviral properties of the tissue product are evaluated and compared to untreated tissues and a reduction in virus titer determined.

Culture Materials

Stock Virus

Rhinovirus type 14 strain 1059 is obtained from the American Type Culture Collection (ATCC), Rockville, Md. (catalogue No. VR-284).

The stock virus is prepared by collecting the supernatant culture fluid from 75%–100% infected culture cells. The cells are disrupted and cell debris removed by centrifugation. The supernatant is removed and may be stored at $\leq -70$ degrees centigrade until use. The supernatant is thawed (if frozen) and centrifuged at 100,000 RPM for 30–60 minutes at approximately 4 degrees centigrade.

The media is removed and the virus is re-suspended in E-MEM test medium outlined below. The virus aliquot may be stored in liquid nitrogen until use or if processed on the day of testing, refrigerated until use in the assay. Immediately prior to testing, the stock virus is titered by 10-fold serial dilution and inoculated in quadruplicate into H1-HeLa cells (also from ATCC catalogue No. CRL-1958) to determine the input virus titer used in the tests.

Cell Cultures

The cells used to determine virucidal activity in this procedure are H1-HeLa cells (also from ATCC Catalogue No. CRL-1958). The medium used to grow the H1-HeLa cells is E-MEM supplemented with 10% FBS and 1% PSG. E-MEM is Minimum Essential Medium (with Earle's salts, non-essential amino acids and without L-glutamine) obtained from Life Technology, Inc. Rockville, Md. (Gibco BRL catalogue No. 10370-021); FBS is Fetal Bovine Serum obtained from Life Technology, Inc. Rockville, M.d (Gibco BRL catalogue No. 16140-071); and PSG is penicillin-streptamine-glutamine obtained from Life Technology, Inc. Rockville, Md. (Gibco BRL catalogue No. 10378-016).

Cultures are maintained and used as monolayers in growth flasks at 36–38 degrees centigrade in a humidified atmosphere of 5%–7% $CO_2$.

Test Medium

The test medium is E-MEM supplemented with 10% Bovine Mucin (Sigma Aldrich Cat. No. M-4503) and 1% PSG. E-MEM is Minimum Essential Medium (with Earle's salts, non-essential amino acids and without L-glutamine) obtained from Life Technology, Inc. Rockville, Md. (Gibco BRL catalogue No. 10370-021); and PSG is penicillin-streptamine-glutamine obtained from Life Technology, Inc. Rockville, Md. (Gibco BRL catalogue No. 10378-016).

Elution Media

The elution media is E-MEM with 1% PSG. E-MEM is Minimum Essential Medium (with Earle's salts, non-essential amino acids and without L-glutamine) obtained from Life Technology, Inc. Rockville, Md. (Gibco BRL catalogue No. 10370-021); and PSG is penicillin-streptamine-glutamine obtained from Life Technology, Inc. Rockville, Md. (Gibco BRL catalogue No. 10378-016).

Method

Preparation of Tissue Product

Samples of the tissue product to be tested are cut into 56±0.5 mm circular discs. The treated tissue discs containing antiviral compositions are utilized in the test and cytotoxicity control parameters. Control tissue discs which do not contain antiviral compositions are included for the positive virus control. The control disc is from the same lot of paper used to prepare the antiviral tissue paper.

Preparation of the Buchner Funnel Filtration Device

Using sterile technique, a pre-weighed disc of tissue paper of varying plies (depending on the tissue product tested) treated with virucide is placed in the bottom portion of each of two Buchner funnels. These will be used for one test replicate and one cytotoxicity control replicate. A disc of pre-weighed untreated tissue will be placed in one 56 millimeter Buchner funnel (Model No. 60240, available from Coors of Golden, Colo.) for use as the positive control.

Using sterile technique, a sterile test tube is inserted into a 250 milliliter filter flask so that the top of the tube rests against the neck of the flask. A rubber stopper is secured onto the outlet stem of the Buchner funnel. The funnel device is placed tightly into the opening of the filtration flask. The outlet stem of the Buchner funnel device is placed tightly into the opening of the filtration flask. The outlet stem of the Buchner funnel is lined up with the opening of the test tube to ensure that anything eluted from the Buchner funnel will be collected in the test tube. One end of a vacuum pump hose is connected to the side arm of the flask.

Treatment With Virus Suspension

An aliquot (500 microliters) of stock virus suspended in E-MEM supplemented with 10% Bovine Mucin (Sigma Aldrich Cat. No. M4503) and 1% PSG is dispensed directly onto the center of the treated tissue discs using a calibrated pipetter. The virus aliquot is allowed to contact the tissue for exactly one (1) minute at room temperature and then immediately collected from the tissue by dispensing 3 milliliters of elution media onto the center region of the disc using a calibrated pipette and immediately applying vacuum suction.

The vacuum suction is applied for 15 seconds while lightly rocking the flask to release any volume caught in the capillaries of the Buchner funnel. The collected virus aliquot in the test tube ($10^{-1}$ dilution) is thoroughly mixed using a vortex mixer, titered by 10-fold serial dilutions (0.3 ml+2.7 ml Elution media) and assayed for the presence of virus. The tissue is removed from the Buchner funnel and a final weight is recorded.

Treatment of Virus Control (Positive Control)

An aliquot (500 microliters) of stock virus suspended in E-MEM supplemented with 10% FBS and 1% PSG is dispensed directly onto the center of the untreated (control) tissue disc using a calibrated pipettor. The virus aliquot is allowed to contact the tissue for exactly one (1) minute at room temperature and then immediately collected from the tissue by dispensing 3 milliliters of E-MEM onto the center region of the disc using a calibrated pipette and immediately applying vacuum suction.

The vacuum suction is applied for 15 seconds while lightly rocking the flask to release any volume caught in the capillaries of the Buchner funnel. The collected virus aliquot is titered as described above. The average virus control titer will be used as a baseline to compare the log reduction of each test parameter following exposure to the products. The tissue is removed from the Buchner funnel and a final weight is recorded.

Infectivity Results

Quantitation of the viral activity of the various filtrates and stock virus is performed by inoculation of each dilution into the appropriate cell cultures in quadruplicate. The end point of a virucidal test for a given tissue is that dilution of virus which infects or is calculated to infect only one of two inoculation wells. This number is defined as the tissue culture infectivity dose or $TCID_{50}$. The results of the virucidal efficacy of a given tissue are given as the "log difference" or percent reduction between the common log of the $TCID_{50}$ result of the treated sample and the $TCID_{50}$ of the untreated sample. The virucidal efficacy of a sample may be derived from the "log difference" in the following manner:

Virucidal Efficacy (in percent)=$(A-B)/A*100$

Where:

$A=TCID_{50}$ (units/ml) from the untreated tissue sample $B=TCID_{50}$ (units/ml) from the treated tissue sample Example Calculation:

$A=10^6$ units/ml $B=10^2$ units/ml

Viral efficacy=$(10^6-10^2)/10^6*100=99.99\%$

The procedure outlined above conforms to standard microbiological assay techniques and yields reliable and reproducible results within the limits of variability associated with such biological experiments.

Measurement of Tissue Panel Softness

Ideally, prior to softness testing, the paper samples to be tested should be conditioned according to Tappi Method #T402OM-88. Here, samples are preconditioned for 24 hours at a relative humidity level of 10% to 35% and within a temperature range of 22° C. to 40° C. After this preconditioning step, samples should be conditioned for 24 hours at a relative humidity of 48% to 52% and within a temperature range of 22° C. to 24° C.

Ideally, the softness panel testing should take place within the confines of a constant temperature and humidity room. If this is not feasible, all samples, including the controls, should experience identical environmental exposure conditions.

Softness testing is performed as a paired comparison in a form similar to that described in "Manual on Sensory Testing Methods", ASTM Special Technical Publication 434, published by the American Society For Testing and Materials 1968 and is incorporated herein by reference. Softness is evaluated by subjective testing using what is referred to as a Paired Difference Test. The method employs a standard external to the test material itself. For tactile perceived softness, two samples are presented such that the subject cannot see the samples, and the subject is required to choose one of them on the basis of tactile softness. The result of the test is reported in what is referred to as Panel Score Unit (PSU).

With respect to softness testing to obtain the softness data reported herein in PSU, a number of softness panel tests are performed. In each test ten practiced softness judges are asked to rate the relative softness of six sets of paired samples. The pairs of samples are judged one pair at a time by each judge: one sample of each pair being designated X and the other Y. Briefly, each X sample is graded against its paired Y sample as follows:

1. a grade of plus one is given if X is judged to be a little softer than Y, and a grade of minus one is given if Y is judged to may be a little softer than X;
2. a grade of plus two is given if X is judged to be a little softer than Y, and a grade of minus two is given if Y is judged to surely be a little softer than X;
3. a grade of plus three is given to X if it is judged to be a lot softer than Y, and a grade of minus three is given if Y is judged to be a lot softer than X; and, lastly:
4. a grade of plus four is given to X if it is judged to be a whole lot softer than Y, and a grade of minus 4 is given if Y is judged to be a whole lot softer than X.

The grades are averaged and the resultant value is in units of PSU. The resulting data are considered the results of one panel test. If more than one sample pair is evaluated then all sample pairs are rank ordered according to their grades by paired statistical analysis. Then, the rank is shifted up or down in value as required to give a zero PSU value to which ever sample is chosen to be the zero-base standard. The other samples then have plus or minus values as determined by their relative grades with respect to the zero-base standard. The number of panel tests performed and averaged is such that about 0.2 PSU represents a significant difference in subjectively perceived softness.

EXAMPLES

Example 1

Table 1 below indicates the virucidal efficacy of virucidal tissues made according to the present invention. Each of the samples were produced via slot extrusion of the virucidal composition onto the fabric side of 1-ply of a cellulosic fibrous substrate as is commonly used in Puffs® Advanced Extra Strength tissue substrate marketed by the instant assignee. The treated substrates were then combined into a 2-ply product (wire side out) and the virucidal efficacy was tested according to the Virucidal Assay Procedure describe above. Preparation of the virucidal composition and each of the samples is outlined below:

Tissue Sample 1

The virucidal composition for this sample was aqueous aluminum sulfate (iron free, approximately 48.8% (wt/wt) $Al_2(SO_4)_3$) available from Holland Company, Incorporated of Adams, Mass.). The solution was then further heated to 120 degrees Fahrenheit and extruded onto the fabric side of 1-ply of a cellulosic fibrous substrate as is commonly used in Puffs® Advanced Extra Strength tissue substrate. The addition rate of the virucidal composition was controlled to produce approximately a 10% by weight add-on of $Al_2(SO_4)_3$ to dry tissue.

Tissue Sample 2

The virucidal composition for this sample was aqueous aluminum sulfate (iron free, approximately 48.8% (wt/wt) $Al_2(SO_4)_3$) available from Holland Company, Inc., Adams, Mass.). The solution was then further heated to 120 degrees Fahrenheit and extruded onto the fabric side of 1-ply of a cellulosic fibrous substrate as is commonly used in Puffs® Advanced Extra Strength tissue substrate. The addition rate of the virucidal composition was controlled to produce approximately a 5% by weight add-on of $Al_2(SO_4)_3$ to dry tissue.

Tissue Sample 3

The virucidal composition for this sample was aqueous aluminum sulfate (iron free, approximately 48.8% (wt/wt) $Al_2(SO_4)_3$) available from Holland Company, Inc., Adams, Mass.). The solution was then further heated to 120 degrees Fahrenheit and extruded onto the fabric side of 1-ply of a cellulosic fibrous substrate as is commonly used in Puffs® Advanced Extra Strength tissue substrate. The addition rate of the virucidal composition was controlled to produce approximately a 2% by weight add-on of $Al_2(SO_4)_3$ to dry tissue.

Tissue Sample 4

The virucidal composition for this sample was made by heating aqueous aluminum sulfate (iron free, approximately 48.8% (wt/wt) $Al_2(SO_4)_3$) available from Holland Company, Inc., Adams, Mass.) to 120 degrees Fahrenheit and thereafter combining Tomadol 25-12 (from Tomah Products Inc., Reserve, La., USA) with a shaft mixer to produce a 48% by weight Aluminum sulfate and 0.5% by weight Tomadol 25-12 solution. The solution was then extruded onto the fabric side of 1-ply of a cellulosic fibrous substrate as is commonly used in Puffs® Advanced Extra Strength tissue substrate. The addition rate of the virucidal composition was controlled to produce approximately a 10% by weight add-on of aluminum sulfate and 0.1% by weight add-on of Tomadol 25-12 to dry tissue.

Tissue Sample 5

The virucidal composition for Tissue Sample 5 was made according to the same procedure utilized for Tissue Sample 4. The only difference was in the add-on level for Tissue Sample 5 whereby the virucidal composition was controlled to produce approximately a 5% by weight add-on of aluminum sulfate and 0.05% by weight add-on of Tomadol 25-12 to dry tissue.

Tissue Sample 6

The virucidal composition for Tissue Sample 6 was made according to the same procedure utilized for Tissue Sample 4. The only difference was in the add-on level for Tissue Sample 6 whereby the virucidal composition was controlled to produce approximately a 2% by weight add-on of aluminum sulfate and 0.02% by weight add-on of Tomadol 25-12 to dry tissue.

Tissue Sample 7

The virucidal composition for this sample was made by heating distilled water to 120 degrees Fahrenheit and thereafter combining in Cupric Sulfate Pentahydrate (Mallinckrodt, Paris, Ky.) with a shaft mixer to produce a 5% by weight Cupric Sulfate aqueous solution. The composition was then extruded onto the fabric side of 1-ply of a cellulosic fibrous substrate as is commonly used in Puffs® Advanced Extra Strength tissue substrate. The addition rate of the virucidal composition was controlled to produce approximately a 0.7% by weight add-on of cupric sulfate on dry tissue.

Tissue Sample 8

The virucidal composition for Tissue Sample 8 was made according to the same procedure utilized for Tissue Sample 7. The only difference was in the add-on level for Tissue Sample 7 whereby the virucidal composition was controlled to produce approximately a 0.35% by weight add-on of cupric sulfate on dry tissue.

Tissue Sample 9

The virucidal composition for Tissue Sample 9 was made according to the same procedure utilized for Tissue Sample 7. The only difference was in the add-on level for Tissue Sample 7 whereby the virucidal composition was controlled to produce approximately a 0.15% by weight add-on of cupric sulfate on dry tissue.

The data from Table 1 show that tissue treated with Aluminum Sulfate alone or with surfactant and Cupric Sulfate alone, were highly virucidal against rhinovirus 14.

TABLE 1

Virucidal efficacy of treated facial tissues against Rhinovirus 14
(Exposure time 1 minute)

| Example No. | Virucidal Composition[a] $Al_2(SO_4)_3$ | Virucidal Composition[a] $CUSO_4$ | Additives[a] Tomadol 25–12 | Virucidal Efficacy % |
|---|---|---|---|---|
| 1 | 11.6 | — | — | ≧99.97 |
| 2 | 7.4 | — | — | 98.53 |
| 3 | 2.8 | — | — | 87.94 |
| 4 | 8.2 | — | 0.08 | 99.54 |
| 5 | 5 | — | 0.05 | 97.40 |
| 6 | 2.6 | — | 0.026 | 97.81 |
| 7 | — | 0.61 | — | 90.56 |
| 8 | — | 0.31 | — | 68.38 |
| 9 | — | 0.15 | — | 64.16 |

[a]Figures are in approximate % chemical addition on air dry tissue.

Example 2

Table 2 below indicates the virucidal efficacy of virucidal tissues made according to the present invention. Each of the samples were produced via slot extrusion of the virucidal composition onto the fabric side of 1-ply of a cellulosic fibrous substrate as is commonly used in Puffs® Advanced Extra Strength tissue substrate. The treated substrates were then combined into a 2-ply product (wire side out) and the virucidal efficacy was tested according to the Virucidal Assay Procedure describe above. Preparation of the virucidal composition and each of the samples is outlined below:

Tissue Sample 1

The virucidal composition for this sample was aluminum sulfate in glycerol. The virucidal composition was prepared by combining 3810 grams of aqueous aluminum sulfate (iron free, approximately 48.8% (wt/wt) $Al_2(SO_4)_3$) available from Holland Company, Inc., Adams, Mass.) and 4000 grams of glycerol (99.77% USP Kosher Stock# 51430, The Procter & Gamble Co., Cincinnati, Ohio) in a 12 liter round bottom flask. The flask and contents were then placed under approximately 30 inches Hg vacuum, heated to 55 degrees Centigrade, and continually stirred via magnetic stir bar for 2 hours.

After 2 hours, the temperature of the mixture was increased to 70 degrees Centigrade and allowed to mix, under vacuum, for another 2 ½ hours. A cold trap was placed between the flask and vacuum pump by attaching a 1 liter round bottom flask in an ice bath which collected a majority of water flashed off of the mixture. Depending on batch variation, an average of 1864 grams of water were collected resulting in a solution concentration of approximately 31.4% aluminum sulfate in glycerol.

The resulting virucidal solution was then transferred to a hot melt glue pumping system, heated to 200 degrees Fahrenheit, and extruded onto the fabric side of 1-ply of a cellulosic fibrous substrate as is commonly used in Puffs® Advanced Extra Strength tissue substrate. The addition rate of the virucidal composition was controlled to produce approximately a 10% by weight add-on of $Al_2(SO_4)_3$ to dry tissue.

Tissue Sample 2

The virucidal composition for Tissue Sample 2 was made according to the same procedure utilized for Tissue Sample 1. The only difference was in the add-on level for Tissue Sample 2 whereby the virucidal composition was controlled to produce approximately a 5% by weight add-on of $Al_2(SO_4)_3$ to dry tissue.

Tissue Sample 3

The virucidal composition for Tissue Sample 3 was made according to the same procedure utilized for Tissue Sample 1. The only difference was in the add-on level for Tissue Sample 3 whereby the virucidal composition was controlled to produce approximately a 2% by weight add-on of $Al_2(SO_4)_3$ to dry tissue.

Tissue Sample 4

The virucidal composition for this sample was aluminum chlorohydrate in glycerol. The virucidal composition was prepared by dissolving 2100 grams aluminum chlorohydrate powder (product AACH-7171, available from Summit Research Labs, Huguenot, N.Y.) into 3900 grams of distilled water and mixing to produce a 35% (wt/wt) solution of aqueous aluminum chlorohydrate. 5052 grams of the 35% AACH-7171 solution was then combined with 3750 grams of glycerol (99.77% USP Kosher Stock# 51430, The Procter & Gamble Co., Cincinnati, Ohio) in a 12 liter round bottom flask.

The flask and contents were then placed under approximately 30 inches Hg vacuum, heated to 55 degrees Centigrade, and continually stirred via magnetic stir bar for 2 hours. After 2 hours, the temperature of the mixture was increased to 70 degrees Centigrade and allowed to mix, under vacuum, for another 2½ to 3 hours. A cold trap was placed between the flask and vacuum pump by attaching a 1 liter round bottom flask in an ice bath which collected a majority of water flashed off of the mixture. Depending on batch variation, an average of 2740 grams of water were collected resulting in a solution concentration of approximately 29.2% Aluminum Sulfate in glycerol.

The resulting virucidal solution was then transferred to a hot melt glue pumping system, heated to 200 degrees Fahrenheit, and extruded onto the fabric side of 1-ply of a cellulosic fibrous substrate as is commonly used in Puffs® Advanced Extra Strength tissue substrate. The addition rate of the virucidal composition was controlled to produce approximately a 10% by weight add-on of MCH-7171 to dry tissue.

Tissue Sample 5

The virucidal composition for Tissue Sample 5 was made according to the same procedure utilized for Tissue Sample 4. The only difference was in the add-on level for Tissue Sample 5 whereby the virucidal composition was controlled to produce approximately a 5% by weight add-on of AACH-7171 to dry tissue.

Tissue Sample 6

The virucidal composition for Tissue Sample 6 was made according to the same procedure utilized for Tissue Sample 4. The only difference was in the add-on level for Tissue Sample 6 whereby the virucidal composition was controlled to produce approximately a 2% by weight add-on of AACH-7171 to dry tissue.

Tissue Sample 7

The virucidal composition for this sample was aluminum zirconium tetra-chlorohydrex glycene in glycerol. The virucidal composition was prepared by combining 3810 grams of aluminum zirconium tetra-chlorohydrex glycene solution (product AZG417, available from Summit Research Labs, Huguenot, N.Y.) and 4000 grams of glycerol (99.77% USP Kosher Stock# 51430, The Procter & Gamble Co., Cincinnati, Ohio) in a 12 liter round bottom flask.

The flask and contents were then placed under approximately 30 inches Hg vacuum, heated to 55 degrees Centigrade, and continually stirred via magnetic stir bar for 2 hours. After 2 hours, the temperature of the mixture was increased to 70 degrees Centigrade and allowed to mix, under vacuum, for another 2½ to 3 hours. A cold trap was placed between the flask and vacuum pump by attaching a 1 liter round bottom flask in an ice bath which collected a majority of water flashed off of the mixture. Depending on batch variation, an average of 1645 grams of water were collected resulting in a solution concentration of approximately 30.9% aluminum zirconium tetra-chlorohydrex glycene in glycerol.

The resulting virucidal solution was then transferred to a hot melt glue pumping system, heated to 200 degrees Fahrenheit, and extruded onto the fabric side of 1-ply of a cellulosic fibrous substrate as is commonly used in Puffs® Advanced Extra Strength tissue substrate. The addition rate of the virucidal composition was controlled to produce approximately a 10% by weight add-on of AZG-417 to dry tissue.

Tissue Sample 8

The virucidal composition for Tissue Sample 8 was made according to the same procedure utilized for Tissue Sample 7. The only difference was in the add-on level for Tissue Sample 8 whereby the virucidal composition was controlled to produce approximately a 5% by weight add-on of AZG-417 to dry tissue.

Tissue Sample 9

The virucidal composition for Tissue Sample 9 was made according to the same procedure utilized for Tissue Sample 7. The only difference was in the add-on level for Tissue Sample 9 whereby the virucidal composition was controlled to produce approximately a 2% by weight add-on of AZG-417 to dry tissue.

The data from Table 1 show that tissue treated with the above described virucidal solutions were highly virucidal against rhinovirus 14.

TABLE 2

Virucidal efficacy of treated facial tissues against Rhinovirus 14
(Exposure time 1 minute)

| Example No. | Virucidal Composition[a] | | | Virucidal Efficacy % |
|---|---|---|---|---|
| | $Al_2(SO_4)_3$ in Glycerol | AACH-7171 in Glycerol | Aluminum Zirconium Chloride Hydroxide Glycine in Glycerol | |
| 1 | 10 | — | — | 99.8415 |
| 2 | 5 | — | — | 99.8415 |
| 3 | 2 | — | — | 80.0474 |
| 4 | — | 10 | — | 99.4988 |
| 5 | — | 5 | — | 90.0000 |
| 6 | — | 2 | — | 0 |
| 7 | — | — | 10 | 94.9881 |

TABLE 2-continued

Virucidal efficacy of treated facial tissues against Rhinovirus 14
(Exposure time 1 minute)

| | Virucidal Composition[a] | | | |
|---|---|---|---|---|
| Example No. | $Al_2(SO_4)_3$ in Glycerol | AACH-7171 in Glycerol | Aluminum Zirconium Chloride Hydroxide Glycine in Glycerol | Virucidal Efficacy % |
| 8 | — | — | 5 | 90.0000 |
| 9 | — | — | 2 | 84.1511 |

[a]Figures are in approximate % chemical addition on air dry tissue.

Referring to Table 3, Panel Softness data is provided comparing a control tissue (i.e.; non-virucidal tissue cellulosic fibrous substrate as is commonly used in Puffs® Advanced Extra Strength tissue) with Tissue Sample 1 of Example 1, from Table I; Tissue Sample 2 of Example 1 from Table I; Tissue Sample 1 of Example 2 from Table 2; and Tissue Sample 2 of Example 2 from Table 2. The Panel Softness data was generated in accordance with the Measurement of Tissue Panel Softness procedure previously described in the instant specification.

As can be seen, the virucidal tissues treated with aluminum sulfate in glycerol are significantly softer than the control tissue. The virucidal tissues treated with aluminum sulfate in glycerol are also significantly softer and as virucidally effective as the virucidal tissues treated with aluminum sulfate only.

TABLE 3

Panel Softness[a] of Treated Facial Tissue

| Control Tissue (PSU) | Control Tissue vs Tissue from Table 1 Example No. 1 (PSU) | Control Tissue vs Tissue from Table 1 Example No. 2 (PSU) | Control Tissue vs Tissue from Table 2 Example No. 1 (PSU) | Control Tissue vs Tissue from Table 2 Example No. 2 (PSU) |
|---|---|---|---|---|
| 0.0 | −1.46 | −1.11 | +1.53 | +1.01 |

[a]Panel Softness data based on 40 comparisons

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An antiviral tissue product, said antiviral tissue product comprising:
   a) a fibrous ply and
   b) an antiviral composition comprising a water soluble metal ion said water soluble metal ion having at least one hydroxide formation constant with a value of at least $10^{12}$.

2. The antiviral tissue product of claim 1 wherein said water soluble metal ion is aluminum, copper, or mixtures thereof.

3. The antiviral tissue product of claim 2 wherein said aluminum is aluminum sulfate, potassium aluminum sulfate, aluminum nitrate, aluminum chlorohydrate, aluminum zirconium tetra-chlorohydrex glycene, or combinations thereof.

4. The antiviral tissue product of claim 2 wherein said copper is copper sulfate, copper chloride, copper nitrate, copper acetate, copper bromide, copper iodide, or mixtures thereof.

5. The antiviral tissue product of claim 1 wherein said antiviral composition further comprises a polyhydric alcohol.

6. The antiviral tissue product of claim 5 wherein said polyhydric alcohol is glycerine.

7. The antiviral tissue product of claim 1 wherein said antiviral composition further comprises an organic acid.

8. The antiviral tissue product of claim 7 wherein said organic acid is a carboxylic acid.

9. The antiviral tissue product of claim 8 wherein said carboxylic acid is pyrrolidone carboxylic acid, citric acid, malic acid, lactic acid, glutaric acid, succinic acid, or combinations thereof.

10. The antiviral tissue product of claim 1 wherein said antiviral tissue product further comprises a lotion.

11. The antiviral tissue product of claim 10 wherein said lotion is polysiloxane.

12. The antiviral tissue product of claim 10 wherein said lotion further comprises an antiviral composition wereby said antiviral composition comprises from about 0.05% to 80% by weight of said lotion and wherein said antiviral composition is a water soluble metal ion.

13. An antiviral tissue product, said antiviral tissue product comprising:
   a first fibrous ply having a first surface and a second surface whereby said second surface is oppositely disposed with respect to said first surface, said first surface comprising an antiviral composition wherein said antiviral composition comprises a water soluble metal ion; said second surface including an antiviral composition wherein said antiviral composition is pyrrolidone carboxylic acid, citric acid, salicylic acid, malic acid, glutaric acid, succinic acid, or mixtures thereof.

14. The antiviral tissue product of claim 13 wherein said water soluble metal ion is aluminum, copper, or mixtures thereof.

15. The antiviral tissue product of claim 13 wherein at least one of said first surface and said second surface further comprises a polyhydric alcohol.

16. A process for making an antiviral tissue product, said process comprising the steps of:
   a) providing a first fibrous ply having a first surface and a second surface whereby said second surface is oppositely disposed with respect to said first surface;
   b) adding an antiviral composition to said first surface of said first fibrous ply wherein said antiviral composition comprises a water soluble metal ion having at least one hydroxide formation constant with a value of at least about $10^7$;
   c) providing a second fibrous ply joined in a face to face relationship with said first fibrous ply, said second fibrous ply having a first surface and a second surface whereby said second surface is oppositely disposed with respect to said first surface, and whereby said second surface of said second fibrous ply faces toward said second surface of said first fibrous ply.

17. The process of claim 15 further comprising adding a polyhydric alcohol to said antiviral composition.

18. The process of claim 15 further comprising adding a lotion to said first surface of at least one of said first fibrous ply and said second fibrous ply.

* * * * *